US006686437B2

(12) United States Patent
Buchman et al.

(10) Patent No.: US 6,686,437 B2
(45) Date of Patent: Feb. 3, 2004

(54) MEDICAL IMPLANTS MADE OF WEAR-RESISTANT, HIGH-PERFORMANCE POLYIMIDES, PROCESS OF MAKING SAME AND MEDICAL USE OF SAME

(75) Inventors: Alisa Buchman, Haifa (IL); Raymond G. Payne, Virginia Beach, VA (US); David G. Mendes, Haifa (IL); Simha Sibony, Naharia (IL); Robert G. Bryant, Lightfoot, VA (US)

(73) Assignee: M.M.A. Tech Ltd., Migdal Haemek (IL)

( * ) Notice: Subject to any disclaimer, the term of this patent is extended or adjusted under 35 U.S.C. 154(b) by 34 days.

(21) Appl. No.: 09/983,182

(22) Filed: Oct. 23, 2001

(65) Prior Publication Data

US 2003/0097182 A1 May 22, 2003

(51) Int. Cl.$^7$ ................................................ C08G 73/10
(52) U.S. Cl. ........................ 528/170; 528/353; 623/16; 623/18.11; 623/66; 623/20; 264/241; 264/250; 264/255; 264/259; 128/898
(58) Field of Search ................................. 528/353, 170; 264/241, 259, 255, 250; 128/898; 623/66, 18.11, 16, 20

(56) References Cited

U.S. PATENT DOCUMENTS

| 4,755,185 A | * | 7/1988 | Tarr | 623/23.4 |
|---|---|---|---|---|
| 4,955,916 A | * | 9/1990 | Carignan et al. | 623/21.16 |
| 5,061,286 A | * | 10/1991 | Lyle | 623/23.63 |
| 5,064,439 A | * | 11/1991 | Chang et al. | 623/66 |
| 5,176,712 A | * | 1/1993 | Homsy | 623/23.36 |
| 5,397,365 A | * | 3/1995 | Trentacosta | 623/18.11 |
| 5,591,233 A | * | 1/1997 | Kelman et al. | 623/23.51 |
| 5,639,850 A | | 6/1997 | Bryant | |
| 5,702,469 A | * | 12/1997 | Whipple et al. | 623/21.15 |
| 5,741,883 A | | 4/1998 | Bryant | |
| 6,048,959 A | | 4/2000 | Bryant | |
| 6,102,952 A | * | 8/2000 | Koshino | 623/20.21 |
| 6,102,955 A | * | 8/2000 | Mendes et al. | 623/20.32 |
| 6,147,135 A | * | 11/2000 | Yuan et al. | 523/105 |

FOREIGN PATENT DOCUMENTS

JP         6098902        11/1991

OTHER PUBLICATIONS

Kawakami et al, "Gas Transfer and In Vitro and In Vivo Blood Compatibility of a Fluorinated Polymide Membrane With an Ultrathin Skin Layer", *Asaio J.*, 42(5):M871–m876, 1996.
Richardson Jr. et al, "Polyimides as Biomaterials: Preliminary Biocompatibility Testing", *Biomaterials*, 14(8):627–635, 1993.
Amstutz, HC, "Biomaterials for Artificial Joints", *Orthopedic Clinics of North America*, 4(2):235–248, 1978.
www.engr.sjsu.edu/cme/materials/projects/srproject/srproj3.html "The Characterization of Particulate Debris Obtained From Failed Orthopedic Implants" Chap. 3.

* cited by examiner

*Primary Examiner*—P. Hampton-Hightower
(74) *Attorney, Agent, or Firm*—G.E. Ehrlich (1995) Ltd.

(57) ABSTRACT

A medical implant having at least a portion thereof made of a formable, pyromellitic, dianhydride (PMDA)-free, non-halogenated, aromatic polyimide is disclosed. Further disclosed are a process of manufacturing the implant and a method of implanting the implant in a subject in need thereof.

49 Claims, 3 Drawing Sheets

MEDICAL IMPLANTS MADE OF WEAR-RESISTANT, HIGH-PERFORMANCE POLYIMIDES, PROCESS OF MAKING SAME AND MEDICAL USE OF SAME

FIELD OF THE INVENTION

The present invention relates to medical implants made in part or in all of formable, pyromellitic, dianhydride (PMDA)-free, non-halogenated, aromatic polyimide, process for manufacturing the implants and method of implanting the implants in subjects in need. More particularly, the present invention relates to orthopedic implants made in part or in all of formable, pyromellitic, dianhydride (PMDA)-free, non-halogenated, aromatic polyimide, process for manufacturing the orthopedic implants and method of implanting the orthopedic implants in subjects in need.

BACKGROUND OF THE INVENTION

Synthetic bio-compatible materials have been used in a wide range of medical and dental applications. Since the earliest uses of gold strands as soft tissue sutures for hernia repairs (around 1000 B.C.), silver and gold artificial dental crowns, and gemstones as tooth replacements (inserted into bone and extending into the oral cavity), bio-compatible materials have evolved to standardized formulations.

Since the late 1930s, high-technology polymeric, ceramic, metallic and composite substrates have played a central role in expanding the application of biocompatible materials-made medical devices.

Plastics hold an important position in the field of medicine as structural materials implanted in the body and as surgical aids. Plastic materials are preferred over metals and ceramics due to their low specific weight, high mechanical strength (as evaluated on a strength-to-weight basis), toughness and chemical inertness and hence stability. Plastic materials are also readily shaped and machined and are commercially available in diverse forms and structures.

Structural plastics are used for permanent endo- or exo-prostheses. Other applications of plastic materials in medicine are blood tubing, heart valves, artificial cornea, artificial heart and kidney components, artificial joints and bone, encapsulants for implanted electrical devices such as pacemakers, flexible circuits, etc.

The advent of orthopedic implants is possibly one of the greatest advances of the past century in orthopedic surgery. The concept of introducing an artificial joint became possible only when new materials and fixation methods were developed and applied by successful collaboration of materials scientists, engineers and surgeons. A joint replacement should have the great advantage of providing pain-free and as smooth as possible movement for the patients, mimicking, as much as possible, the functionality and movements repertoire of the respective natural joint.

In the case of an endo-prosthesis, where two bearing surfaces are replaced by artificial prostheses (made of either similar or different materials), thus creating an artificial joint, high friction and wear problems may occur over a period of time, depending, to a great extent, on the patient's activity.

In the orthopedic joint endo-prosthesis[1], three basic conditions are necessary for successful total arthroplasty: (i) bio-compatibility with the surrounding tissues; (ii) good adhesion and stable fixation of the endo-prosthesis to the bone; and (iii) negligible friction without formation of wear debris of the joint elements during service under dynamic load. Large frictional forces in the hinged joint and tendency of the implant material to spall and delaminate can cause loosening of the construction and creation of wear debris, which lead to acute or chronic inflammation.

A natural joint is a connection between two bones and is classified in two fundamental types[16]: (i) joints lacking a joint cavity, which allow little or no movement, for example the joint between adjacent vertebrae and the joint between the ribs and sternum; and (ii) joints having a joint cavity, which constitute the freely movable joints of the body, and are called the synovial joints. Depending on their position in the body, synovial joints have evolved to permit one or more of the following types of movements: flexion, extension, abduction, adduction, rotation and circumduction. In the human body, there are six kinds of synovial joints: ball and socket, hinge, pivot, ellipsoidal, saddle and gliding.

Continuous friction and accelerated wear of two contacted non-lubricated surfaces moving one with respect to the other are the result of the interaction of asperities or surface roughness. When two surfaces are rubbed together under load, asperities on the two surfaces may adhere, and relative sliding movement will then be possible only if the adhesive forces are overcomed by shear forces. Unless the shearing takes place exactly along the original interface, material will be removed, resulting in what is known as adhesive wear.

Cyclic variations under load, or cyclic movements of a bearing under constant load, impose dynamically varying stresses on the elements of the material. Such dynamically varying stresses may cause fatigue fractures at, or close to the surface, thereby promoting particle detachment. This process is known as fatigue wear.

Lubrication minimizes frictional resistance between bearing surfaces by keeping them apart. Fluid and boundary lubrication[17] are probably the most important mechanisms preventing cartilage wear under high loads in natural joints. It will be appreciated in this respect that, the coefficient of friction in a synovial joint is about 0.001–0.01, while typical dry coefficient of friction of plastic on plastic is about 0.1–0.3 and for metal on metal about 0.3–0.8, rendering these materials poor substitutes.

Several families of materials such as polymers, metals, ceramics and composite materials were tested as potential implant materials for hip and knee arthroplasty. Due to the harsh environment of the human body fluids and the frequent movement of these parts, the useful lifetime of these implants is about less than 10 years. Thus, a replacement implant is needed which involves repeated (once or more) surgery (depending on the age and activity of the patient). Fractures and wear of the implant are clearly observed. The wear debris produced by friction from the damaged implants circulate in the body or stay in the tissues and cause inflammation. In order to solve this problem a low friction, wear-resistant material is needed.

The majority of total hip prostheses currently implanted consists of a hard metal, or ceramic femoral head placed against a cross-linked or uncross-linked ultra-high-molecular weight-polyethylene (UHMWPE) acetabular cup with or without cement fixation. Currently, more than 500,000 artificial hips are implanted annually, worldwide. The low-friction, low-wear un-crosslinked UHMWPE has been considered for the last two decades as the best polymeric solution for total artificial hip implants. Notwithstanding the success, over the last 10 years these prostheses exhibited frequent failures, due to late aseptic loosening, creep, migration and inflammation, resulting in the need to be revised through surgery. No implant survived more than 25 years, while most of the implants lasted less than 10 years, typically 5 to 7 years.

The following materials have been used to form artificial medical implants over the years:

Teflon®[2] is a material known to cold flow, namely, irreversibly deform over time under loading. It failed due to mechanical wear (80%), infection (10%) and metal femoral head penetration, absorption of great masses of the surrounding bone and implanted material.

Silicone[14] prostheses are used in finger and toe joints. Fatigue fractures occurrence and the low durability of this material results in weak bonding which leads to particles release.

UHMWPE[3–5] promotes bone lysis (Periprosthetic Osteolysis) due to release of submicron size debris into the surrounding soft tissues as a result of wear. The body reacts by "activating" macrophages that attack the particles and release biochemical mediators in the bone implant interface, causing inflammation and loosening. The UHMWPE implant degrades in the body, chips off, exposes the base metal and becomes released from the cemented fixation. There are 20–30% cases of failure within 5–7 years of implantation that call for replacement.

Cross-linked UHMWPE[2] is a new modified version of UHMWPE which shows less wear than UHMWPE, thus longer term of service, but still has a risk of wear debris stimulated osteolysis. There is a risk of post oxidation of the UHMWPE by the Gamma irradiation during the cross-linking process, releasing free radicals. This oxidation weakens the material and causes embrittlement during aging. UHMWPE is stiffer and more prone to water absorption which would affect the mechanical properties and tribology of the material.

Ceramic implants[6] are composed of Alumina and Zirconia and are mostly used in Europe. Ceramic has excellent bio-compatibility, good surface finish, low friction and hence low wear and high hardness. The drawbacks of ceramic implants are low fracture toughness, low impact strength and brittleness-causing fragmentation and cracking of the implants. Failures include femoral head fractures and catastrophic breakage of ceramic sockets. Improved performance greatly depends upon careful surgical techniques with precise positioning of the prosthesis. Failure to correctly position this type of implant results in massive wear and the onset of osteolysis between the femoral neck and the rim of the acetabular cup. Small sharp edged particles (5 micron) and smaller granular debris (0.4 microns) have been found in macrophages near the surface of the implant. Zirconia wear debris is more frequent than that of alumina. Osteolysis appeared after a mean implantation time of 92 months. Loosening and migration of acetabular components were also found, which required replacement. The ceramic wear debris stimulates a foreign body response. Other disadvantages of ceramics are the high specific density (causing elevated weight of the implant compared to plastics) and accelerated stress hydrolysis in humid environment once the surface is violated through mechanical stress causing crack formation in wet environment and fracture (stress corrosion).

Metal implants[5–7] consist mostly of CoCrMo alloy which exhibits low wear (40–100 times lower than UHMWPE), good surface finish and high mechanical properties. The drawbacks of metals are metallic electrochemical corrosion risk (low bio-compatibility) accelerated by the ions present in the body fluids and the presence of oxygen. These conditions generate chemically active and toxic degradation products, and produce wear particles. The wear particles are very small (mostly 10–25 nm in diameter) but the number of particles exceeds those of UHMWPE (10 to 500 times more). The small size and large number of the particles raise a new issue of remote distribution in the human body and the biologically effects on various cells and tissues. Some particles may even attach or dissolve in the lymphatic vessels. The hematological spread of the metal particles may access any tissue in the body, such as liver, kidney and even the brain. Metal debris in the lymph nodes causes structural changes including necrosis and fibrosis. There is an increased risk of development of tumors of the lymphatic system (carcinogenic potential). The level of inflammation depends on the amount, size and shape of the debris.

Hyper-sensitivity of the body to metal ions release is another problem. Metal ions may bind to body proteins when they are released from the metal implant. Metal ions bound to proteins induce T lymphocyte response leading to hypersensitivity reactions. Another problem is the toxicity of the metal ions (Co and Cr). Co and Cr ions, which reduce cell viability even at low concentrations, are toxic to osteoblast cells by inhibiting their differentiation. Titanium is a much lighter metal but is a poor bearing material. It wears fourfold more than CoCr and is toxic as well. It activates macrophages and causes osteolysis. Compared to polymers, metal prostheses are substantially heavier.

Composite material implants such as polymer mixed with glass or carbon fibers have been tested as implant material without success. Glass fibers deteriorate at humid environment and carbon fibers tend to circulate, causing inflamation. The surface of such implants is not smooth because of the fibers which cause porosity. Presently, such composite materials are not used as implants.

Polyimides:[15],[20]

It is known that aromatic polyimides (PI) form an important class of high performance polymers because of their many desirable characteristics such as: mechanical strength, low dielectric constant, good processability, e.g., in processes such as injection or compression molding, wear and radiation resistance, chemical inertness, e.g., inertness to solvents, good adhesion properties, low thermal expansion (as a plastic), thermal stability and long term durability. PI with desired properties can be produced by manipulation of both monomer selection and process engineering. Thus, there is a wide scope of applications for PI, including; aerospace, microelectronics, optoelectronics, fiber optics, etc.

There are known PIs, such as, for example, Kapton®, (which is fabricated as a film and cannot be molded) and Vespel® (which can be molded) that integrate pyromellitic dianhydride (PMDA) group as one of their monomers. This chemical moiety (the PMDA group) which is integrated within the polymer chain by displacement of the oxygen of the two anhydride groups (forming an imide bond) is susceptible to hydrolysis. Since it is hydrolizable, it could rapidly degrade in the body, especially under wear and friction.

Amstutz[19] has suggested using Vespel® (a PMDA-containing aromatic polyimide compound) as a possible bearing material for orthopedic use. It was compared to UHMWPE (creeps and deforms under load+cold flows) and to Teflon® (severe wear and cold flow). Vespel® has the same density and same modulus as bone, has good elasticity and damping of shock forces, has high strength to weight ratio, can be molded and machined and has sufficient wear and creep resistance. However, toxicological aspects have never been tested. Furthermore, due to the presence of a PMDA group in Vespel®, this material is likely to undergo hydrolysis in the body, especially under wear and friction conditions.

Due to this shortcoming, the PI polymers which contain the PMDA group, are not applicable in orthopedic implantation procedures. However, these PIs have been used as implants in other, less demanding, medical and clinical applications as described hereinafter.

Among the known PMDA-containing PIs and PIs which contain halogens and aliphatic units that are used as implants in non-orthopedic medical applications, are:
1. KAPTON®[12]2. HUGHES HR 610®[9]
2. DuPont 2555®[9]
3. Hitachi PIQ®[9]
4. M&T 2056/5000®[9]
5. DuPont SP1®[9]
6. DuPont SP21®+15% graphite[10]
7. Amoco AI® (Polyimide-Amide)[10]
8. 6FDA-DDS®[13]

(IM-PH-C(CF$_3$)$_2$-PH-IM-PH-SO$_2$-PH)n

9. 6FDA-6FAP®(13)

(IM-PH-C(CF$_3$)$_2$-PH-IM-PH-S(CH$_3$)$_2$-PH)n 10. 6FDA-APPS®[13]

(IM-PH-C(CH$_3$)$_2$-PH-IM-PH-O—SO$_2$-PH-O-PH)n

11. SILTEM1500®[12]

IM-O-IM-(CH$_2$)$_3$—Si—(CH$_3$)$_2$—)n —O—Si(CH$_3$)$_2$—(CH$_2$)$_3$-IM-O-IM-PH-CH$_2$-PH

12. ULTEM 1010®[12]
13. Polyimide film[18]
wherein in the above compounds, IM=imide group; and PH=Phenylene group.

The above listed polyimides are biocompatible but have not or cannot be used in load bearing applications. Furthermore, they have some prominent disadvantages which render them unsuitable for implants for use in orthopedic procedures. For example, Kapton® cannot be molded into a solid article and it contains PMDA (which, as stated above, is susceptible to hydrolysis). Ultem®, which is not wholly aromatic, has relatively poor wear and fracture toughness properties. The "SP" systems (Vespel®) are PMDA-based and, consequently are, susceptible to hydrolysis (same structure as Kapton® which is base etched). The Hitachi PIQ® is a photoresist material applicable in electronic applications and cannot be used as a polyimide medical bearing material.

As far as non-orthopedic medical applications are concerned, Kapton® is used as flexible substrate in neuro-prosthesis devices for functionally interfacing parts of the nervous system. This micro-implant is used to assist neurological disorder. Although it was proved to be biocompatible with the human body[7], it is not used in a mechanical load bearing application.

Polyimides (e.g., 2–5 as listed above), were also used as substrates in sensory and neural structure of the cochlea. Four kinds of PIs were implanted in cat cochleas for 3 months. Histological findings showed that all four PIs were bio-compatible with mild or no inflammatory reaction to the implant. Any change was limited to the immediate vicinity of the implant[8].

Polyimide SP-21 with 15% graphite (Du Pont) was implanted into the abdominal cavity and paravertebral muscle of mongrel dogs for up to 3 years. Histological examinations showed that the PI was biocompatible with minimal tissue reaction. Local hemorrhage was noticed and no surface deterioration was visible. Weight gain after 3 years implantation was 1.45% [9], as expected when PMDA is present and the hydrolysis problem is accounted for.

A flexible electrode made of polyimide was used as an intraocular retinal prosthesis implanted in eyes. This device stimulates artificially surviving ganglion cells to replicate. The polyimide used (Kapton®), was proved as bio-compatible and non-toxic[10], but not as load bearing.

Kapton® and other polyimides were checked for blood compatibility in order to be used as encapsulants for bio-sensors. They were chosen because of their strong adherence to metal oxides and their organic solvent resistance. Biocompatibility was tested in vitro on level I and II. The tests included cell culture toxicity, protein absorption, clotting times and haemolysis. No cytotoxicity or haemolysis were detected, protein absorption and clotting time were close to the results obtained from the control. The following three different polyimides were tested: Kapton®, Ultem®, and Siltem® (siloxane-PEI). Kapton® showed the best biocompatibility. These results suggest that polyimides are attractive candidates as biosensor encapsulants[11].

Further evidence of polyimides bio-compatibility to blood was provided by tests for cardiopulmonary bypass and extracorporeal gas exchange membrane oxygenator, used for neonatal respiratory failure. Blood compatibility tests were performed by inserting polymer tubes into peripheral veins of mongrel dogs for 7 days. The tested polyimides showed excellent in vitro blood compatibility. Platelets hardly changed shape, and deformation and aggregation were not detected. Adsorption of plasma protein on the surface of the polyimide was negligible. No thrombus formation or fibrin precipitation were observed on the polyimide.

Considering the above described teachings, there appears to be a great need for an artificial orthopedic implant that could withstand the natural properties of the joint, thus overcoming the above problems and limitations. Furthermore, the increasing need of implanting hip prostheses in younger, more active patients, demands the development of new artificial hip joints using alternative, more advanced, suitable materials. In addition, the material to be chosen for orthopedic endo-prosthesis implantation should withstand the different loads, and resist friction and wear conditions of the human hip or knee joints. This new generation of materials should further provide a solution to late aseptic loosening, and to lesser debris generation in order to increase the duration of survival of implants.

SUMMARY OF THE INVENTION

It is an object of present invention to provide an implant, made, in part or in all, of formable, pyromellitic, dianhydride (PMDA)-free, non-halogenated, aromatic polyimide, for use in medical applications, in particular in orthopedic implantations, as well as other applications, such as, but not limited to, dental applications and cardiovascular applications.

It is a further object of the present invention to provide a process of producing a medical implant made, in part or in all, of formable, pyromellitic, dianhydride (PMDA)-free, non-halogenated, aromatic polyimide.

It is still a further object of the present invention to provide a method of implanting a medical implant made, in part or in all, of formable, pyromellitic, dianhydride (PMDA)-free, non-halogenated, aromatic polyimide.

It is yet a further object of the present invention to provide a permanent endo- and/or exo-prostheses made, in part or in all, of formable, pyromellitic, dianhydride (PMDA)-free, non-halogenated, aromatic polyimide, a process of producing same and a method of implanting same.

It is another object of the present invention to provide a an implant for joint replacement, a process of producing same and a method of implanting same.

It is yet another object of present invention to provide implants applicable in orthopedic implantation, having a high level of bio-compatibility with the surrounding tissues, strong and stable fixation of the endo-prosthesis to the bones and substantial reduction of friction and wear debris of the joint elements under dynamic load.

It is yet an additional object of present invention to provide a prosthesis that is resistant to varying stresses that may cause fatigue or wear fractures at, or close to its surface, which may result in particle detachment.

It is yet a further object of the present invention to provide a bio-compatible orthopedic implants having an extended functional lifetime, thus minimizing the need for revisions and replacements.

These and other objects of the invention will become clearer as the description proceeds.

Hence, according to one aspect of the present invention there is provided a medical implant comprising at least a portion made of a formable, pyromellitic, dianhydride (PMDA)-free, non-halogenated, aromatic polyimide.

According to another aspect of the present invention there is provided a process of producing a medical implant having at least a portion made of a formable, pyromellitic, dianhydride (PMDA)-free, non-halogenated, aromatic polyimide, the process comprising providing the polyimide in a form selected from the group consisting of powder form, granule form, pellet form and plate form; and forming the polyimide provided in the form into a predetermined desired shape. The polyimide may be formed in a net shape.

According to further features in preferred embodiments of the invention described below, forming the polyimide is effected by molding.

According to still further features in the described preferred embodiments molding is effected at a temperature ranging from about 25° C. to about 500° C.

According to still further features in the described preferred embodiments molding is further effected at a pressure ranging from about 100 PSI to about 20,000 PSI. According to yet another aspect of the present invention there is provided a method of implanting a medical implant in a subject, the method comprising providing a medical implant having at least a portion made of a formable, pyromellitic, dianhydride (PMDA)-free, non-halogenated, aromatic polyimide; and implanting the medical implant in the subject.

As used herein throughout, the term "subject" refers to any animal having a vertebrae, mammals in particular, including human-beings.

According to further features in preferred embodiments of the invention described below, the medical implant is an orthopedic implant.

According to still another aspect of the present invention there is provided a method of treating a disorder associated with orthopedic malformation and/or disfunction and wherein an implantation of artificial implant is needed, in a subject in need of such treatment, comprising implanting in the subject an implant having at least a portion thereof made of a formable, pyromellitic, dianhydride (PMDA)-free, non-halogenated, aromatic polyimide.

According to an additional aspect of the present invention there is provided a method of treating a damaged or degenerative arthroplasty associated with malformation and/or disfunction of a joint, and wherein an implantation of an artificial joint implant is needed, in a subject in need of such treatment, comprising implanting in the subject an artificial joint implant made of formable, pyromellitic, dianhydride (PMDA)-free, non-halogenated, aromatic polyimide. Hence, in a one embodiment of the invention, the medical implant is a joint replacement prostheses.

According to further features in preferred embodiments of the invention described below, the joint is selected from the group consisting of a joints lacking a joint cavity and a synovial joint.

According to still further features in the described preferred embodiments the synovial joint is selected from the group consisting of a ball and socket joint, a hinge joint, a pivot joint, an ellipsoidal joint, a saddle joint and a gliding joint.

According to still further features in the described preferred embodiments the synovial joint is selected from the group consisting of a hip joint, a knee joint, an ankle joint, a shoulder joint, an elbow joint, a wrist joint, a finger joint, a finger metacarpal joint, a toe joint, a toe-metatarsal joint and a carpo-metacarpal joint.

According to still further features in the described preferred embodiments the entire medical implant is made of the polyimide. According to still further features in the described preferred embodiments the medical implant is selected from the group consisting of a permanent endo-prostheses and a permanent exo-prostheses.

According to still further features in the described preferred embodiments the medical implant further comprising a portion made of at least one other material.

According to still further features in the described preferred embodiments the other material is selected from the group consisting of polymers such as UHMWPE, crosslinked UHMWPE and polysulfones; ceramics such as zirconia and aluminum oxide; metals such as stainless steel, titanium alloys and Co—Cr alloys; materials coated with wear resistance substances including diamond and hardened metals; and the like.

According to still further features in the described preferred embodiments the polyimide has the formula (I):

wherein:

Y and Z are each independently selected from the group consisting of a chemical bond between two adjacent aromatic rings, O, CO and substituted phenyl, where Y and Z can be linked to any free position on the adjacent aromatic ring;

X is selected from the group consisting of substituted allyl, vinyl, acetynyl, phenylethynyl and benzocyclobutenyl; and n represents an integer equal to or greater than 1, preferably n ranges from about 1 to about 100.

According to still further features in the described preferred embodiments X is selected from the group consisting of benzocyclobutenyl, acetynyl and phenylethynyl; Y and Z are each independently selected from the group consisting of a chemical bond between two adjacent aromatic rings and O; n represents an integer ranging from about 10 to about 100; and X, Y, and Z being linked to the adjacent aromatic rings in the 3, 3', 4 and 4' positions.

The present invention successfully addresses the shortcomings of the presently known configurations by providing a medical implant made, in part or in all, of a formable, pyromellitic, dianhydride (PMDA)-free, non-halogenated, aromatic polyimide, having a high level of bio-compatibility with surrounding tissues, substantial reduction of friction and wear debris under dynamic load, resistant to varying stresses that may cause fatigue or wear fractures at, or close to its surface, having an extended functional lifetime and in all having a performance that far exceeds that of other known materials traditionally used in medical implants.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DETAILED DESCRIPTION OF THE INVENTION

The present invention is of (i) a medical implant made, in part or in all, of formable, pyromellitic, dianhydride (PMDA)-free, non-halogenated, aromatic polyimide; (ii) a process of manufacturing a medical implant made, in part or in all, of formable, pyromellitic, dianhydride (PMDA)-free, non-halogenated, aromatic polyimide; and (iii) a method of implanting a medical implants made, in part or in all, of formable, pyromellitic, dianhydride (PMDA)-free, non-halogenated, aromatic polyimide. The medical implant of the present invention can be used in orthopedic applications, as well as many other applications, including for example, dental applications and cardiovascular applications, in which an implant or portions thereof are subject to friction and wear forces.

The principles and operation of a medical implant according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The inventors of the present invention have unexpectedly found that formable, pyromellitic, dianhydride (PMDA)-free, non-halogenated, aromatic polyimide thermosetting compounds possess the long searched for distinguished properties required for implantation in orthopedic procedures.

As is discussed in length in the preceding Background section, PMDA-containing polyimides, such as Vespel®, are susceptible to hydrolysis, especially under wear and friction.

From a practical point of view, the only way to prevent the presence of the PMDA group is not to use PMDA as a monomer in the polymerization process of synthesizing a polyimide polymer. Consequently, any medical implant made, in part or in all, of a formable, pyromellitic, dianhydride (PMDA)-free, non-halogenated, aromatic polyimide thermosetting compound is within the scope of present invention.

A preferred embodiment of the present invention relates to the use of a formable, pyromellitic, dianhydride (PMDA)-free, non-halogenated, aromatic polyimide thermosetting compound of the formula (I):

A formable, pyromellitic, dianhydride (PMDA)-free, non-halogenated, aromatic polyimide which is particularly suitable for implementing the present invention is MP-1 supplied by M.M.A. TECH Ltd., Post Office Box 73, Mifalei Haemek, 23100 Migdal Haemek, Israel. The formable, pyromellitic, dianhydride (PMDA)-free, non-halogenated, aromatic polyimides described herein, and MP-1 in particular, are highly suitable for use in medical implants because such polyimides are free of the shortcomings and limitations characterizing (PMDA)-containing polyimides and other materials used in medical implants. The polyimides used in the context of the present invention, and the MP-1 polyimide in particular, has a chemical structure that confers an implant made therefrom both distinguished mechanical strength and prominent resistance to degradation resulting from friction or wear and biodegradation resulting from exposure to body fluids. In addition, the polyimides used in the context of the present invention, and the MP-1 polyimide in particular, are low friction, resistant to radiation and oxidation, non-hydrolizable and can be used against surfaces made therefrom or from metal or a ceramic material.

Consequently, unlike other plastics or polyimides, using a formable, pyromellitic, dianhydride (PMDA)-free, non-halogenated, aromatic polyimide, MP-1 in particular, in medical implants will minimize or totally prevent revision implant surgery.

MP-1 is supplied in the form of an ingot. If so desired, it may be further treated and purified. For implant production it can be provided as rod stock and then machined to a (I)

wherein:
  Y and Z are each independently selected from the group consisting of a chemical bond between two adjacent aromatic rings, O, CO and substituted phenyl, where Y and Z can be linked to any free position on the adjacent aromatic ring, preferably, Y and Z are each independently selected from the group consisting of a chemical bond between two adjacent aromatic rings and O;
  X is selected from the group consisting of substituted allyl, vinyl, acetynyl, phenylethynyl and benzocyclobutenyl, preferably, X is selected from the group consisting of benzocyclobutenyl, acetynyl and phenylethynyl; and
  n represents an integer equal to or greater than 1, preferably n ranges from about 1 to about 100, more preferably, from about 10 to about 100.

In a presently preferred embodiment, X, Y, and Z are linked to the adjacent aromatic rings in the 3, 3', 4 and 4' positions.

Formable, pyromellitic, dianhydride (PMDA)-free, non-halogenated, aromatic polyimide and methods for their synthesis are described in the following publications: U.S. Pat. Nos. 6,048,959; 3,179,614, 3,179,631 and 3,179,634 and further in Polyimides, ed. by D Wilson, H.D. Stenzenberger and P. M. Hergenrother, Blackie and Sons LTD (1990),. London and Glasgow, all of which are incorporated by reference as if fully set forth herein.

desired shape. It is then sterilized (preferably in heat) and ready for implantation. For larger masses of production a special mold can be used for compression molding of net-shaped parts to avoid machining. Standard molding can be used, with temperatures ranging from about 25° C. to above 400° C. and pressures ranging from several hundred to several thousand PSI, depending on the exact type of polyimide and on the geometry of the part produced therefrom.

One main goal for future applications of biocompatible materials made devices is to extend their functional life-span, so that the need for revisions and replacements be minimized.

As mentioned hereinbefore, the polyimides used in context of the present invention, including MP-1, are particularly useful as materials for implants in orthopedic procedures. Consequently, the various arthroplasty procedures are discussed hereinafter in some details.

Total joint arthroplasty is an operation on a joint, where the bones are reshaped and replaced to restore motion to the joint and function to the muscles and ligaments and other soft tissue structures that control the functionality of the joint. The operation is indicated in individuals with a painful, disabling arthritic joint that is no longer responsive to conservative treatment.

Presently used artificial prosthetic joints fail mainly because of wear and loosening of the articulating surfaces.

All variety of materials, such as plastics, metallics, ceramics and alike, which are currently in use in manufacturing the prosthetic components do wear. The wear particles are miniature and measure from submicron to a few microns in size. Many types of particles provoke tissue reaction, which by release of biochemical mediators, affects the bone that hosts the implant, resulting in bone absorption and loosening of the joint implant.

Loosening, fracture and wear, eventually causes pain and necessitates a new operation—a revision. The more extensive is the bone absorption, the more difficult is the surgical procedure that necessitates the use of larger implants to accommodate for the lost bone and bone graft to replace bone loss. The prognosis for success and longevity of the implant after revision operation is less predictable and much depends, among other factors, on the quality of the available bone.

The Implant (Prosthesis):

The implant is designed with a close resemblance to the native joint that it replaces. It has articulating components which simulate the native articulation.

Some of the components have a stem or a peg which enhances their fixation to bone. Others fit into or onto the bone which is surgically shaped to receive them.

Orthopedic implants of superior shapes are disclosed in, for example, U.S. Pat. Nos. 5,580,353; 5,824,099; 6,102,955; 6,159,246; EP Patent Application No. 96302382.5, GB Patent No. 2301032; and IL Patent No. 109344, all of which are incorporated herein by reference.

Materials:

Combination of ultrahigh molecular weight polyethylene articulating with metal is the most widely used. The metal used to be stainless steel, but has mostly changed into stronger alloys based on cobalt chromium. Fixation of the components to bone is achieved by polymethylmethacrylate cement. Alternatively, fixation is achieved by creating porous surface of the metal, that allows bone ingrowth. This is done by technologies such as plasma spray or coating the metal or plastic with a porous layer of active calcium phosphate ceramics such as hydroxyapatite or tricalcium phosphate. A different technology achieves a porous layer of titanium powder or a titanium net on the plastic.

The combinations of the articulating parts varies. These are polyethylene against metal, or polyethylene against ceramics such as alumina or zirconia, or metal against metal such as cobalt alloy, or ceramic against ceramic such as alumina.

The articulating components are distinguished by their tribological properties, friction, lubrication and wear. Friction depends on the coefficient property of the material, the diameter of the component from the center of motion and the surface finish quality. Lubrication is the property of the synovial fluid, which is known to be deficient after surgical arthroplasty. Wear is the property of the two articulating surfaces and depends, among other factors, on the sphericity, surface finish, surface energy and lubrication. It is related to friction but not proportionally.

Coupling stainless steel or cobalt alloy with polyethylene is presently considered the state-of-the-art. However, in about 10 years of function, it may produce in excess of 1 mm of linear wear, that results in the astronomical number of tens of billions or more of particles, during that period of function. Coupling titanium alloy with polyethylene results in a large amount of wear of both the plastic and the titanium due to the inadequate existing polishing technology.

Coupling ceramic with polyethylene results in about 50% decrease of wear in comparison to metal and polyethylene, which is a significant improvement but still causes release of billions of particles during same period of time. The experience of coupling metal with metal is still uncertain, since past experience with that combination, though with less sophisticated technology, was poor. The experience with coupling ceramic with ceramic is still too short to conclude.

Wear Particles:

The kind and intensity of the biological reaction to wear particles depends mainly on their physical, but also on their chemical properties. Three types of polyethylene particles are distinguished: chunks, flakes and granules. It is the granules of about one micron in size that are responsible for the intense inflammatory reaction. The histology is characterized by macrophages, which swallow the particles by the process of phagocytosis, but are unable to digest the non-biological plastic, and by giant cells that result from conglomeration of macrophages. The inflammatory process results in large granulomata and is accompanied by release of biochemical mediators such as prostaglandins and interleukins, that cause absorption of the host native bone. Wear of other plastics such as acetal-copolymer is physically similar, but may cause even more intensive reaction.

Metallic wear is characteristically of small granules which are swallowed by round macrophages without formation of giant cells but the biochemical reaction is similar to the one caused by plastics.

Ceramic wear is also of small granules and provokes similar reaction to metallic wear.

Anatomy and Biomechanics:

Peripheral joints are (di)-arthroidal. They have two or three articulating surfaces of hyaline cartilage that share the load and transfer it to the adjacent bone. The joint cavity is bordered by a synovial membrane, that originates from the margins of the joint cartilage. The cavity is sealed off by the joint capsule that is reinforced by capsular ligaments. The synovial cells excrete fluid that together with diffused interstitial fluid nourishes and lubricates the joint cartilage and the joint capsule and ligaments.

The load transmitted physiologically through the articulating surfaces in the joints of the lower extremity may reach the magnitude of 3 to 7 times body weight. The cause for these high loads are the lever effect of the muscles which stabilize and move the joints. The loads are distributed and absorbed by the bones and soft tissue that forms the joint complex. They are partly further transferred to the adjacent structures and joints.

The particular peripheral joints which undergo total joint arthroplasty are the hip joint, knee, ankle, shoulder, elbow and wrist. Other joints which are less commonly done are the fingers and metacarpals, the toes and the metatarsals, the carpo-metacarpal and the non-arthroidal vertebral joints.

Description of the Native Joints:

The hip joint is made of two components—the pelvic acetabulum that articulates with the femoral head and neck, making the so-called ball and socket joint.

The knee joint is made of three components—the femoral condyles, the tibial plateau and the patella, that make a complex motion of rolling, sliding and rotating.

The ankle joint is made of three components—the tibia, the talus and the fibula, that make a complex motion mainly of sliding and rotation.

The shoulder joint is made of two components—the scapula glenoid and the head of the humerus, that make a complex motion with a very large range.

The elbow joint is made of three components—the condyles of the humerus, the trochlea of the ulna and the head of the radius, that make a complex motion of sliding and rotation.

The wrist joint is made of four components—the radius, ulna, scaphoid and lunate.

The finger joints and toe joints are made of two components—the head of a phalanx and the base of another phalanx.

The metacarpals and metatarsals joints are made of two components similarly to the fingers joints.

The carpo metacarpal joint is made of one or two components—trapezius and the base of first metacarpus, which form a saddle joint.

The vertebral joint is basically a disc unit with no joint cavity.

Design of Components:

The basic principles of design of prosthetic joints are as follows:

Similarity to the anatomy of the components of the native joint.

Adequate mechanical properties of the joint such as size and stability.

Adequate mechanical properties of the materials such as strength, stiffness and resistance to cold flow.

Adequate tribological properties of the materials such as low friction and wear resistance.

Adequate kinesiological properties such as range of motion.

Figure 1A:
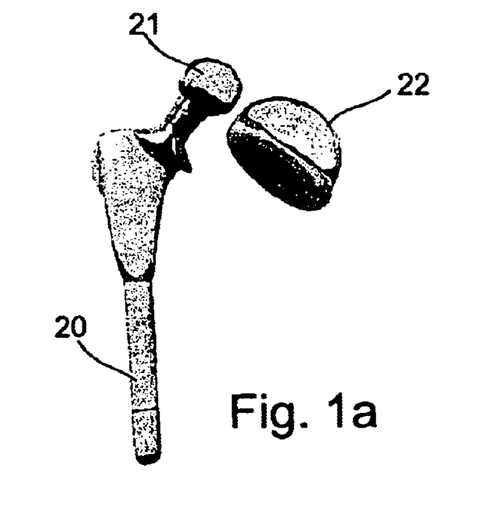
FIGS. 1a–b show a hip joint implant made, at least in part, of formable, pyromellitic, dianhydride (PMDA)-free, non-halogenated, aromatic polyimide according to the present invention.
Figure 1B:
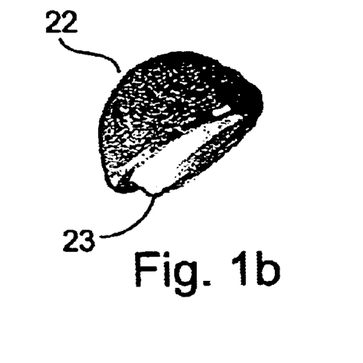

Specific Implant Designs:

Total hip joint implant: A total hip joint implant is basically composed of two to four components: stem 20, head 21, cup 22 and insert 23 (FIGS. 1a–b). One part of the articulating surfaces, namely, the cup or the insert inside the cup, is conventionally made of polymer such as ultra-high-molecular weight-polyethylene (UHMWPE).

As described above for the total hip joint implant, in all the following list of artificial joints, one part of the articulating components is conventionally made of high density polyethylene. For different joints the articulating surfaces may be composed of two or three (such as the knee) components.

Figure 2:
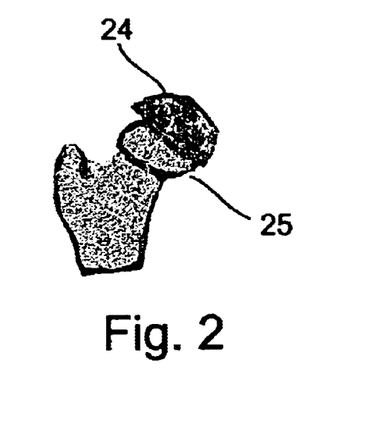
FIG. 2 shows a hip joint resurfacing implant made, at least in part, of formable, pyromellitic, dianhydride (PMDA)-free, non-halogenated, aromatic polyimide according to the present invention.

Hip joint resurfacing implant: is basically composed of two components: acetabular 22 and head 25 (FIG. 2).

Figure 3:
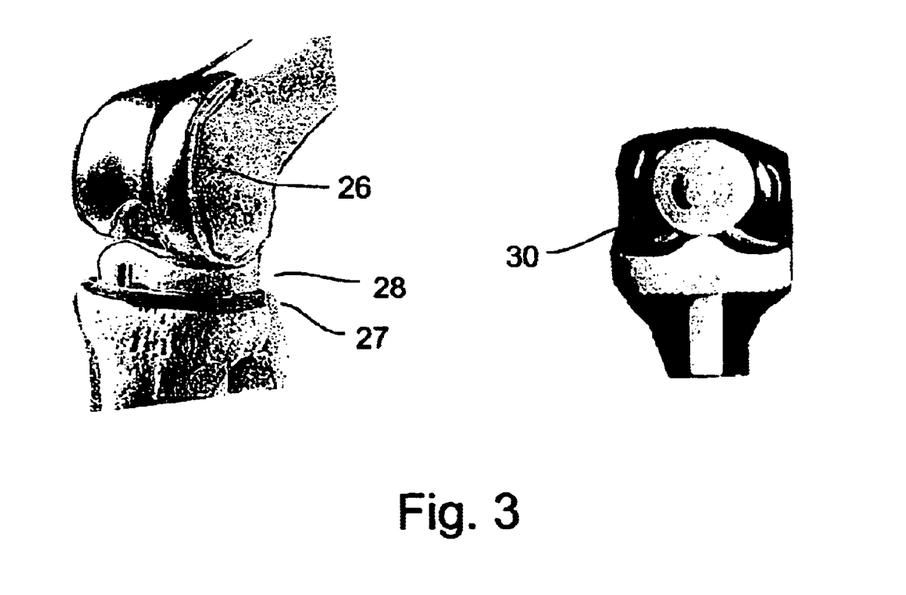
FIG. 3 shows a total knee joint implant made, at least in part, of formable, pyromellitic, dianhydride (PMDA)-free, non-halogenated, aromatic polyimide according to the present invention.

Total Knee joint implant: is basically composed of three to four components: femoral 26, tibial tray 27, tibial insert 28 and patella 30 (FIG. 3).

Figure 4:
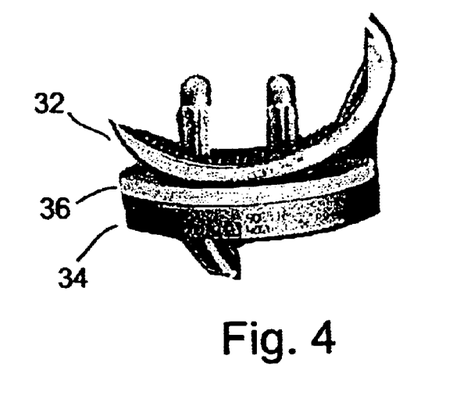
FIG. 4 shows a uni condylar replacement implant made, at least in part, of formable, pyromellitic, dianhydride (PMDA)-free, non-halogenated, aromatic polyimide according to the present invention.

Uni condylar replacement implant: is basically composed of two to three parts: condyle 32, tibial tray 34 and insert 36 (FIG. 4).

Figure 5:
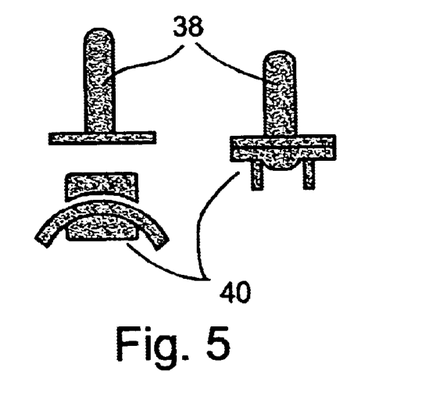
FIG. 5 shows an ankle joint implant made, at least in part, of formable, pyromellitic, dianhydride (PMDA)-free, non-halogenated, aromatic polyimide according to the present invention.

Ankle joint implant: is basically composed of two components: tibial 38 and talar 40 (FIG. 5).

Figure 6:
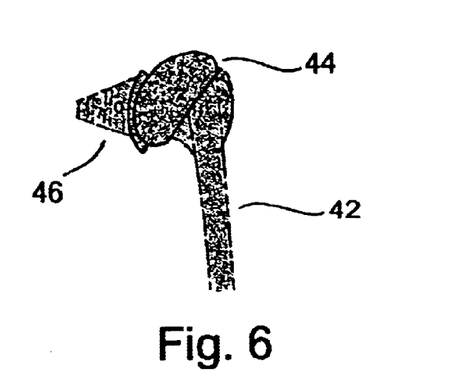
FIG. 6 shows a shoulder joint implant made, at least in part, of formable, pyromellitic, dianhydride (PMDA)-free, non-halogenated, aromatic polyimide according to the present invention.

Shoulder joint implant: is basically composed of two or three components: stem 42, head 44 and glenoid 46 (FIG. 6).

Figure 7:
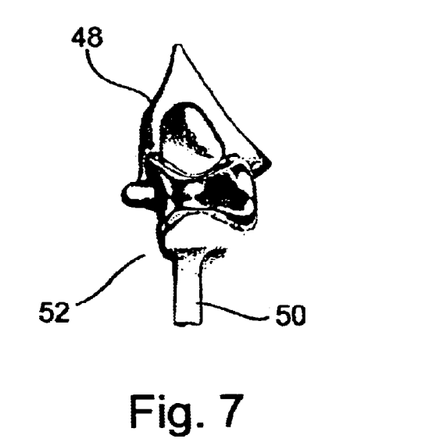
FIG. 7 shows an elbow joint implant made, at least in part, of formable, pyromellitic, dianhydride (PMDA)-free, non-halogenated, aromatic polyimide according to the present invention.

Elbow joint implant: is basically composed of three components: humeral 48, ulnar 50 and radial 52 (FIG. 7).

Figure 8:
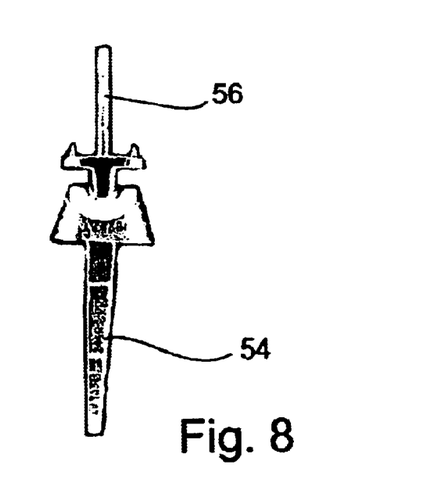
FIG. 8 shows a wrist joint implant made, at least in part, of formable, pyromellitic, dianhydride (PMDA)-free, non-halogenated, aromatic polyimide according to the present invention.

Wrist joint implant: is basically composed of two or more components: radial 54, carpal 56 and lunate 58 (FIG. 8).

Figure 9:
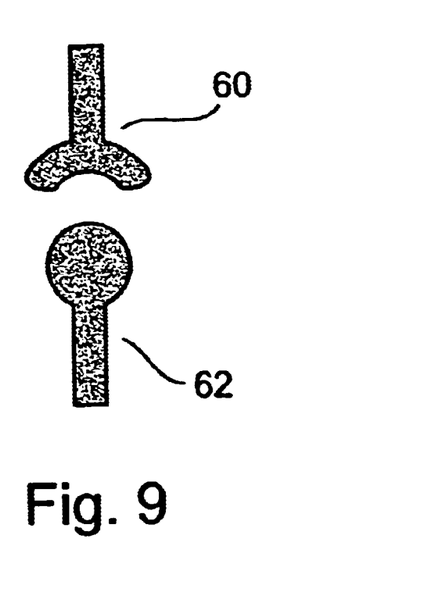
FIG. 9 shows fingers and toes implants made, at least in part, of formable, pyromellitic, dianhydride (PMDA)-free, non-halogenated, aromatic polyimide according to the present invention.

Fingers and toes implants: are basically composed of two components 60 and 62 (FIG. 9).

Metacarpal and metatarsal joint implants: are basically composed like fingers and toes implants.

Figure 10:
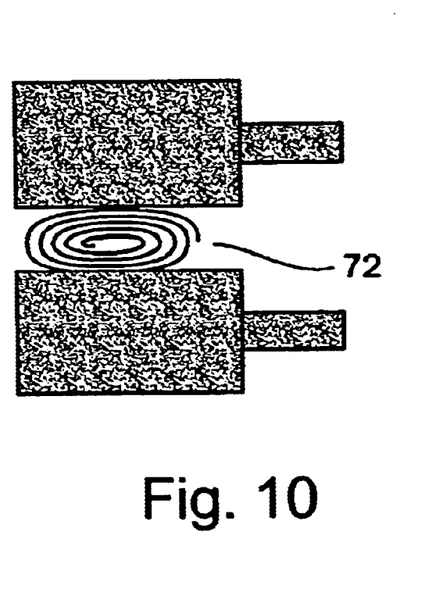
FIG. 10 shows a vertebral disc unit implant made, at least in part, of formable, pyromellitic, dianhydride (PMDA)-free, non-halogenated, aromatic polyimide according to the present invention.

Vertebral disc unit implant: is basically composed of one component 72 (FIG. 10).

According to preferred embodiments of the present invention, the formable, pyromellitic, dianhydride (PMDA)-free, non-halogenated, aromatic polyimide, MP-1 in particular, replaces either the high density polyethylene (thermoplastic or cross-linked) or one side (or face) of the articulating components. Orthopedic implants made of formable, pyromellitic, dianhydride (PMDA)-free, non-halogenated, aromatic polyimide, MP-1 in particular, according to the present invention may be used in, for example, the following, non-exhaustive list of applications:

(a) For replacing entirely each of the above described bones. Replacing bones is a possibility, for example, in case of resection of a bone tumor (b) For replacing part of the above described bones. When replacing articulations of joints, for example, parts of the above described bones are replaced.

(c) For use as an articulating component formable, pyromellitic, dianhydride (PMDA)-free, non-halogenated, aromatic polyimide, MP-1 in particular, is used according to the present invention as an articulating component in total replacement of joints with artificial implants. Formable, pyromellitic, dianhydride (PMDA)-free, non-halogenated, aromatic polyimide, MP-1 in particular, can be used in association with additional materials.

The formable, pyromellitic, dianhydride (PMDA)-free, non-halogenated, aromatic polyimide, MP-1 in particular, can be used in non-orthopedic applications as well, in, for example, cardiovascular implants such as valves, stents, temporomandibular joint (TMJ) and maxillofacial implants for example masticatory systems, bone tissue replacement, endosseous implants, etc., and as housing of implants such as pacemakers.

Surgical Procedures:

The surgical procedures are similar for all joints. They involve removal of the diseased parts of the joint, that is the damaged cartilage and adjacent bone, and replacing them with artificial parts which closely resemble in structure and/or function the removed native parts.

The artificial parts fit onto the reshaped bone and are fixed either with bone cement (e.g., polymethylmethacrylate) and press fit of the part, or by self-anchorage with bone ingrowth to its porous surface.

The design of the artificial parts may include a stem, a keel or pegs, which fit onto the medullary canal of the bone or into a hole pre-prepared in the bone. An artificial part may fit loosely and be fixed with bone cement, press-fit for self-anchorage or include extendible anchors which are retracted upon placement and extended thereafter so as to secure the implant in place.

Following fixation of the components, the joint is reduced and the soft tissue tension is appropriately checked to reassure stability of the joint.

According to a preferred embodiment of the present invention, the articulating surfaces of an implant are made of a formable, pyromellitic, dianhydride (PMDA)-free, non-halogenated, aromatic polyimide material, MP-1 in particular, replacing the high density polyethylene or other materials used in the formation of articulating surfaces. Conventionally, all articulating surfaces in the joints are made of same material, such as ceramic or metal alloy. Consequently, the formable, pyromellitic, dianhydride (PMDA)-free, non-halogenated, aromatic polyimide material, MP-1 in particular, replaces one or more components while the articulating counterpart could be made of the same material, ceramics, metal alloy or composite material.

The low rate of wear of a formable, pyromellitic, dianhydride (PMDA)-free, non-halogenated, aromatic polyimide material, MP-1 in particular, significantly reduces the production of wear particles, and hence is expected to reduce or eliminate the granulomatous reaction and the resulting absorption of bone and to significantly prolong the implant's service-span.

Examples of Implants:

For the variety of different joints, the formable, pyromellitic, dianhydride (PMDA)-free, non-halogenated, aromatic polyimide, MP-1 in particular may be used as one of the articulating components.

The Cup for Total Hip Joint:

The cup is cemented into the acetabulum of the patient.

Alternatively, the cup may have a peripheral porous surface coating made of materials such as titanium powder and/or hydroxyapatite powder.

Alternatively, the cup may be made of two components: a metal back and an insert made of the formable, pyromellitic, dianhydride (PMDA)-free, non-halogenated, aromatic polyimide material, MP-1 in particular, used in the present invention.

The cup for hip joint resurfacing may be prepared as described for the total hip joint.

The Tibial Part and the Patella Part in Total Knee Joint:

The tibial part may be cemented in bone.

Alternatively, the tibial part may have a peripheral porous surface coating made of materials such as titanium powder and/or hydroxyapatite powder.

Alternatively, the tibial part may be made of two components: a metal tray and an insert made of the polyimide used in the present invention.

The Glenoid Part for the Shoulder Joint:

The same procedure as described for total hip joint may be applied. The same description is for other joints, as well.

MP-1 and its Advantages:

As is mentioned hereinabove, the most common polymer currently used for orthopedic implants is UHMWPE. Table I below summarizes the properties of this polymer compared to those of MP-1.

TABLE I

Properties of polyimide MP-1 vs. UHMWPE

| UHMWPE | Polyimide MP-1 |
|---|---|
| 1. Does not promote bacterial growth | 1. Does not promote bacterial growth |
| 2. Excellent chemical resistance. | 2. Excellent chemical resistance. |
| 3. Not a high performance engineering material. | 3. A novel ultrahigh performance engineering material. |
| 4. Has been used for a long time also as an implant. | 4. So far used only for specific applications: hot-wet environments, high speed conditions, electronics, advanced composites and high voltage applications. |
| 5. The wear particles cause a major damage requiring revision surgery. | 5. No detectable wear particles. |
| 6. Polyethylene creeps (low Tg), low thermal stability | 6. Does not cold flow or creep (very high Tg), excellent thermal stability. |
| 7. The properties are direct function of molecular weight (MW) and not inter-chain interaction - this leads to 5 and 6. | 7. The properties are a function of cross-linking and chemistry. There is very high inter-chain interaction which leads to a material that has excellent toughness, low creep, high cross-linking, and can replace metals in many applications. |
| 8. Low thermal properties, must be sterilized by radiation or gas. | 8. High thermal properties, can be sterilized by heating to 250° C. (cost-effective procedure). |
| 9. Oxidizes upon radiation | 9. Is not effected by radiation |
| 10. Needs surface finish by polishing or heat melting. | 10. Minimal (if any) surface finish is required. |

Being a member of the above defined formable, pyromellitic, dianhydride (PMDA)-free, non-halogenated, aromatic polyimide family, MP-1 offers several design advantages over stainless steel, titanium, ceramics and UHMWPE, acetal, polyamides and PMDA-containing aromatic polyimides.

Among its advantages are: it can be compression molded, it is not hydrolysable, it is tougher and maintains its dimensional stability, it is not effected by ions and has high impact strength and can function well with other materials under dynamic loads.

MP-1 has a higher tensile modulus, 590 KSI, compared to many other engineering plastics, for example: Teflon®-150 KSI, UHMWPE-180 KSI.

It offers superior resistance to chemicals, steam, moisture, radiation and can be easily sterilized by heat. MP-1 can maintain high mechanical properties even at temperatures reaching 350° C.

The polymer's self inherent hardness reduces friction and wear. This property helps prevent implants from cavitating on the bone. Stiffness and impact performance are close to those of the bone tissue and function in concert with the skeletal structure.

Radio-translucence permits complete implant inspection by X-ray and MP-1's non-porous structure and density (1.4 g/cc versus water and tissue ~1 g/cc) permit inspection by ultrasound.

Bearing Properties of MP-1

The need for dry bearings, gears, sliders and other dynamic parts in the general industry, in military and aerospace applications is ever-growing. The demands for these applications involve elevated temperatures and pressures at high velocities. Hence, the material requirements are: inherent hardness, self-lubricity, high impact strength, wear and corrosion resistance, durability at vibrations, lightweight, high specific strength and moderate cost. MP-1 performs reliably over extended periods of time, under these extreme, stringent conditions which makes it an excellent solution for radical conditions found in a biological environment.

MP-1 performs well in continuous sliding applications, and is better than UHMWPE in all modes of wear: abrasion, fretting, rotation and reciprocation. MP-1 has been tested as a bearing material at 260° C. and at 2000 cycles/min, 55 lb. Force at rotation of 15 deg.

It should be noted that UHMWPE and its derivatives, ceramics and metals cannot adhere directly to any substrate without an intermediate material (primer) or special harsh surface pretreatment, while MP-1 can be mould as a liner and adheres excellently with high durability bond.

In view of its properties non-medical uses of MP1 include mechanical parts such as gears, bearings and valves, advanced composites with carbon or ceramic fibers and fillers for structural applications, high strength adhesive for high temperature application such as bonding diamonds and graphite, board material for printed circuits, matrix for molded ceramics for a wide range of applications, etc.

MP-1 can replace metals in structures that demand light weight and high mechanical strength. Is used as infrastructure components for nuclear power stations and in aerospace applications.

The present invention provides new medical applications for formable, pyromellitic, dianhydride (PMDA)-free, non-halogenated, aromatic polyimide, MP-1 in particular. More specifically, it was found by the inventors that this material is particularly useful in the production of new implants for hip, knee, elbow, shoulder, finger, toes, spine, dental prosthetics, temporomandibular Joint (TMJ) and maxilofacial implants, pacemaker components, heart valves, stents, pumps and hinge units.

While a presently preferred embodiment of the present invention relates to orthopedic implants, there is no intention to limit the invention to such implants as the formable, pyromellitic, dianhydride (PMDA)-free, non-halogenated, aromatic polyimide used in context of the present invention is highly suitable in other applications such as, but not limited to dental and cardiac applications. The polyimide compounds used in context of the present invention is a wear- and abrasion-resistant material and is therefore best suited for use in articulating components of orthopedic and other implants. In contrast to PMDA-containing aromatic polyimides, the formable, pyromellitic, dianhydride (PMDA)-free, non-halogenated, aromatic polyimide is used in context of the present invention as a bio-compatible in-vivo load bearing material. Distinguished and unique physico-chemical properties of the polyimide of the invention, confer implants and parts made therefrom and which are subject to service-wear forces, performance that far exceeds that of other known materials traditionally used in such medical applications.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Biocompatibility Test:

MP-1 has passed the standard bio-compatibility test according to ISO 10993–1.

Abrasion Test:

Abrasion test was devised on a 2 mm thick plate of MP1 compared to stainless steel D2 60 RC (martensite). The test was carried out in an abrasion testing machine where the sample was abraded against an abrasion wheel WA60K7V, 6" diameter, ⅜" wide, coated with white alumina with ceramic binder, open structure, medium grain. The velocity was 200 cycles per minute, at a load of 800 grams for a period of 380 minutes.

The parameters tested were the change in weight, depth of the wear trace, and looking for wear debris using SEM.

Results showed that for MP1 there was no detectable weight loss, the surface became shiny, wear volume was less than 0.01 $mm^3$, and no wear debris were found even at a 5,000 magnification of SEM.

D2 60 RC showed, in the same abrasion test, a groove of 0.135 mm with wear volume of 0.56 $mm^3$ and with wear debris flakes of 5 microns.

Using MP-1 as an Implant in Orthopedic Procedures:

In joint replacement such as the hip joint the artificial implant is made of two or more parts. These are divided into the fixation components that are introduced in bone, and are traditionally made of metal alloy, and articulating components that are presently made of a variety of materials such as polymers, ceramics and metals. MP-1 is the material of choice for the articulating components because of its mechanical properties. The cup made of MP-1 is introduced into the acetabulum following appropriate reaming of the acetabular bone. It is fixed in the pelvic acetabulum in a spatial orientation of 45° from the horizontal and at an angle of anteversion of 10°. Fixation in bone is done with bone cement. Alternatively, a porous surface is created on the periphery of the cup with metallic granules such as titanium and/or with hydroxyapatite granules. The size of the pores range from approximately 100 to 300 microns. With this porous surface, the cup is introduced to press fit in place. The stem component is then introduced into the prepared femoral canal and the head is placed over the conical neck. Then the joint is reduced and the head is situated stably within the cup. Following closure of the operative wound, the joint may gradually return to full function. This procedure is described for animal experimental study as well as for human clinical use.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

CITED REFERENCES

1. A. Movshovich, G. I. Roitberg, Meditsinskaya Tekhnika, No.5, pp.15–19 (1974)
2. Durasul—Polyethylene, Sulzer Orthopedics Ltd. (Internet site).
3. K. Mann, D. L. Bartel, T. M. Wright, A. H. Burstein, J. of Biomechanics, 28 (9), 1067 (1995).
4. L. Ambrosio, et al., J. of Mat. Sci. (Mat. in Medicine), 7, 723 (1996).
5. E. Ingham, J. Fisher, Proc. Instn. Mech. Engrs., 214 part H, 21 (2000). (A review).
6. L. M. Jazrawi, M. D. Bogner, et al., J. of Arthoplasty, 14 (7), 781 (1999).
7. H. L. Amssian, et al. Acta Orthopedica, Scand 70 (6), 578 (1999).
8. T. Stieglitz, J. U. Meyers, Med.Dev.Technol. 10(6):28–30 (1999).
9. H. S. Haggerty, H. S. Lusted, Acta Otolaryngology, 107 (1–2), 13 (1989).
10. H. C. Amstutz, M. Lodwig, J. Biomedical Materials Res., 10 (1),25 (1976).
11. R. A. Jesinger, V. l. Stonick, IEEE Engineering in Medicine, Int. Conf. Proc. San Diego (1993).
12. R. R. Richardson, J. A. Miller, W. M. Richert Biocompatible materials, 14 (3), 627 (1993).
13. H. Kawakami, S. Nagaoka, S. Kubota, ASAIO J. 42(5), M871 (1996).
14. C. Harlan, M. D. Amstutz, Orthopedic Clinics of North America, 4 (2), 235 (1978).
15. "Polyimides" by M. K. Ghosh, K. M. Mittal, Marcel Dekker Inc., NY, Chap. 19, 20 (1996).
16. C. P. Anthony, G. A. Thilbodean, Text book of Anatomy and Physiology, $10^{th}$ Edi., Mosby Publ. London, 170 (1979).

17. Wright, Dowson, J. Anatomy, 121 (1), 107 (1976).
18. Implantable polyimide, JP-1991000334164 (Dec. 4, 1994).
19. H. C. Amstutz, J. Biomedical Materials Res., 3, 547 (1968).
20. Robert G. Bryant, High Perform. Polym. 8, 607–615 (1996).
21. Polyimides ed by D Wilson, H. D. Stenzenberger and P. M. Hergenrother. Blackie and sons LTD (1990) London and Glasgow.

What is claimed is:

1. A medical implant comprising at least a portion made of a formable, pyromellitic, dianhydride (PMDA)-free, non-halogenated, thermosetic aromatic polyimide.

2. The medical implant of claim 1, wherein the entire medical implant is made of said polyimide.

3. The medical implant of claim 1, wherein the medical implant is an orthopedic implant.

4. The medical implant of claim 3, wherein the medical implant is selected from the group consisting of: a permanent endo-prosthesis and a permanent exo-prosthesis.

5. The medical implant of claim 3, wherein the medical implant is a joint replacement phosthesis.

6. The medical implant of claim 1, further comprising a portion made of at least one other material.

7. The medical implant of claim 6, wherein said at least one other material is selected from the group consisting of polymers, ceramics, metals and materials coated with a wear resistance substance.

8. The medical implant of claim 1, wherein said polyimide has the formula (I):

wherein:

Y and Z are each independently selected from the group consisting of a chemical bond between two adjacent aromatic rings, O, CO and substituted phenyl, where Y and Z can be linked to any free position on the adjacent aromatic ring;

X is selected from the group consisting of substituted allyl, vinyl, acetynyl, phenylethynyl and benzocyclobutenyl; and n represents an integer equal to or greater than 1.

9. The medical implant of claim 8, wherein n is between 1–100.

10. The medical implant of claim 8, wherein:

X is selected from the group consisting of benzocyclobutenyl, acetynyl and phenylethynyl;

Y and Z are each independently selected from the group consisting of a chemical bond between two adjacent aromatic rings and O;

n represents an integer between 10 and 100; and

X, Y, and Z being linked to the adjacent aromatic rings in the 3, 3', 4 and 4' positions.

11. The medical implant of claim 8, wherein the medical implant is an orthopedic implant.

12. The medical implant of claim 11, wherein the medical implant is selected from the group consisting of a permanent endo-prosthesis and a permanent exo-prosthesis.

13. The medical implant of claim 11, wherein the medical implant is a joint replacement prosthesis.

14. The medical implant of claim 8, further comprising a portion made of at least one other material.

15. The medical implant of claim 14, wherein said at least one other material is selected from the group consisting of polymers, ceramics, metals and materials coated with a wear resistance substance.

16. A process of producing a medical implant having at least a portion made of a formable, pyromellitic, dianhydride (PMDA)-free, non-halogenated, thermosetic, aromatic polyimide, the process comprising:

providing said polyimide in a form selected from the group consisting of: powder form, granule form, pellet form and plate form; and said polyimide provided in said form into a net shape, comprising at least a portion or said polyimide.

17. The process of claim 16, wherein the entire medical implant is made of said polyimide.

18. The process of claim 16, wherein forming said polyimide is by compression molding.

19. The process of claim 18, wherein said molding is effected at a temperature ranging from about 25° C. to about 500 0° C.

20. The process of claim 19, wherein said molding is further effected at a pressure ranging from 100 PSI to 20,000 PSI.

21. The process of claim 16, wherein the medical implant is an orthopedic implant.

22. The process of claim 21, wherein the medical implant is selected from the group consisting of a permanent endo-prosthesis and a permanent exo-prosthesis.

23. The process of claim 21, wherein the medical implant is a joint replacement prosthesis.

24. The process of claim 16, wherein said polyimide has the formula (I):

wherein:
Y and Z are each independently selected from the group consisting of a chemical bond between two adjacent aromatic rings, O, CO and substituted phenyl, where Y and Z can be linked to any free position on the adjacent aromatic ring;
X is selected from the group consisting of substituted allyl, vinyl, acetynyl, phenylethynyl and benzocyclobutenyl; and
n represents an integer equal to or greater than 1.

25. The process of claim 24, wherein n ranging from about 1 to about 100.

26. The process of claim 24, wherein:
X is selected from the group consisting of benzocyclobutenyl, acetynyl and phenylethynyl;
Y and Z are each independently selected from the group consisting of a chemical bond between two adjacent aromatic rings and O; and
n represents an integer ranging from about 10 to about 100; and
X, Y, and Z being linked to the adjacent aromatic rings in the 3, 3', 4 and 4' positions.

27. A method of implanting a medical implant in a subject, the method comprising:
providing a medical implant having at least a portion made of formable, pyromellitic, dianhydride (PMDA)-free, non-halogenated, thermosetic, aromatic polyimide; and
implanting the medical implant in the subject.

28. The process of claim 27, wherein the entire medical implant is made of said polyimide.

29. The method of claim 27, wherein the medical implant is an orthopedic implant.

30. The method of claim 29, wherein the medical implant is selected from the group consisting of: a permanent endo-prosthesis and a permanent exo-prosthesis.

31. The method of claim 29, wherein the medical implant is a joint replacement prosthesis.

32. The method of claim 27, wherein the medical implant comprises a portion made of at least one other material.

33. The method of claim 32, wherein said at least one other material is selected from the group consisting of polymers, ceramics, metals and materials coated with a wear resistance substance.

34. The method of claim 27, wherein said polyimide has the formula (I):

(I)

wherein

Y and Z are each independently selected from the group consisting of a chemical bond between two adjacent aromatic rings, O, CO and substituted phenyl, where Y and Z can be linked to any free position on the adjacent aromatic ring;

X is selected from the group consisting of substituted allyl, vinyl, acetynyl, phenylethynyl and benzocyclobutenyl; and
n represents an integer equal to or greater than 1.

35. The method of claim 34, wherein n is ranging from about 1 to about 100.

36. The method of claim 34, wherein:
X is selected from the group consisting of benzocyclobutenyl, acetynyl and phenylethynyl;
Y and Z are each independently selected from the group consisting of a chemical bond between two adjacent aromatic rings and O;
n represents an integer ranging from about 10 to about 100; and
X, Y, and Z being linked to the adjacent aromatic rings in the 3, 3', 4 and 4' positions.

37. The method of claim 34, wherein the medical implant is an orthopedic implant.

38. The method of claim 37, wherein the medical implant is selected from the group consisting of a permanent endo-prosthesis and a permanent exo-prosthesis.

39. The method of claim 37, wherein the medical implant is a joint replacement prosthesis.

40. The method of claim 34, wherein said medical implant comprises a portion made of at least one other material.

41. The method of claim 40, wherein said at least one other material is selected from the group consisting of polymers, ceramics, metals and materials coated with a wear resistance substance.

42. A method of treating a disorder associated with orthopedic malformation and/or disfunction and wherein an implantation of artificial implant is needed, in a subject in need of such treatment, the method comprising implanting in said subject an implant having at least a portion thereof made of a formable, pyromellitic, dianhydride (PMDA)-free, non-halogenated, thermosetic, aromatic polyimide.

43. The process of claim 42, wherein the entire medical implant is made of said polyimide.

44. A method of treating a damaged or degenerative arthroplasty associated with malformation and/or disfunction of a joint, and wherein an implantation of an artificial joint implant is needed, in a subject in need of such treatment, the method comprising implanting in said subject an artificial joint implant made of formable, pyromellitic, dianhydride (PMDA)-free, non-halogenated, thermosetic, aromatic polyimide.

45. The process of claim 44, wherein the entire medical implant is made of said polyimide.

46. The method of claim 44, wherein said joint is selected from the group consisting of a joints lacking a joint cavity and a synovial joint.

47. The method of claim 46, wherein said synovial joint is selected from the group consisting of: a ball and socket joint, a hinge joint, a pivot joint, an ellipsoidal joint, a saddle joint and a gliding joint.

48. The method of claim 46, wherein said synovial joint is selected from the group consisting of a hip joint, a knee joint, an ankle joint, a shoulder joint, an elbow joint, a wrist joint, a finger joint, a finger metacarpal joint, a toe joint, a toe-metatarsal joint and a carpo-metacarpal joint.

49. A medical implant comprising at least a portion made of a formable, pyromellitic, dianhydride (PMDA)-free, non-halogenated, thermosetic, aromatic polyimide, said medical implant being sterile-packaged.

* * * * *